US00PP33577P2

(12) United States Plant Patent
Nelson et al.

(10) Patent No.: US PP33,577 P2
(45) Date of Patent: Oct. 26, 2021

(54) STRAWBERRY PLANT NAMED 'BG-12.3241'

(50) Latin Name: *Fragaria ananassa*
Varietal Denomination: BG-12.3241

(71) Applicant: BERRY GENETICS, INC., Freedom, CA (US)

(72) Inventors: Steven D. Nelson, Watsonville, CA (US); Michael D. Nelson, Watsonville, CA (US); Leo W. Stoeckle, Moorpark, CA (US)

(73) Assignee: Berry Genetics, Inc., Freedom, CA (US)

( * ) Notice: Subject to any disclaimer, the term of this patent is extended or adjusted under 35 U.S.C. 154(b) by 0 days.

(21) Appl. No.: 16/990,801

(22) Filed: Aug. 11, 2020

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./208
CPC ..... A01H 6/7409
See application file for complete search history.

*Primary Examiner* — Anne Marie Grunberg
(74) *Attorney, Agent, or Firm* — Foley & Lardner LLP

(57) ABSTRACT

This invention relates to a new and distinct variety of strawberry plant named 'BG-12.3241'. This new strawberry plant named 'BG-12.3241' is primarily adapted to the growing conditions of the central coast of California, and is primarily characterized by its red fruit color, medium fruit size, and cordate fruit shape; very good fruit flavor, very firm fruit flesh, with seeds held even with the surface; very smooth fruit surface, even color, with only a slight difference between primary and secondary fruit; medium plant size, upright in habit, with medium to sparse density; medium yellow green foliage color, and medium foliage size; and fruit trusses typically held level with to above the plant, with medium pubescence.

5 Drawing Sheets

Latin name of the genus and species of the plant claimed: *Fragaria ananassa.*

Variety denomination: 'BG-12.3241'.

BACKGROUND OF THE INVENTION

The present invention relates to a new and distinct strawberry variety named 'BG-12.3241'. This new variety is a result of a controlled cross made in 2012 in an ongoing breeding program between strawberry selection designated 'BG-6.3001' (unpatented) as the seed (female) parent, and strawberry variety designated 'BG-959' (U.S. Plant Pat. No. 17,864) as the pollen (male) parent. The variety is botanically known as *Fragaria ananassa.*

The seedling resulting from the aforementioned cross was selected from a controlled breeding plot in Ventura County, Calif. in the winter of 2014. After its selection, the new variety was asexually propagated by stolons in both Siskiyou County, Calif. and San Joaquin County, Calif. The new variety was extensively tested over the next several years in fruiting fields in Ventura County, Calif. This propagation has demonstrated that the combination of traits disclosed herein as characterizing the new variety are fixed and remain true-to-type through successive generations of asexual reproduction.

BRIEF SUMMARY OF THE INVENTION

'BG-12.3241' is primarily adapted to the climate and growing conditions of the central coast of California. The nearby Pacific Ocean provides the humidity and moderate temperatures needed to produce a strong, vigorous plant and maintain fruit quality during the winter and spring production months.

The following traits have been repeatedly observed and are determined to be unique characteristics of 'BG-12.3241', which in combination distinguish this strawberry plant as a new and distinct variety:

1. Fruit is red in color, medium in size, and cordate in shape;
2. Fruit has very good flavor, very firm flesh, with seeds held even with the surface;
3. Fruit surface is very smooth, even in color, with only a slight difference between primary and secondary fruit;
4. Plant is medium in size, upright in habit, with medium to sparse density;
5. Foliage is medium yellow green in color, and medium in size; and
6. Fruit trusses are typically held level with to above the plant, with medium pubescence.

The strawberry variety that is believed to be most closely related to the new variety 'BG-12.3241' is 'INSPIRE' (U.S. Plant Pat. No. 29,794). In side-by-side comparisons to the similar strawberry variety 'INSPIRE', 'BG-12.3241' differs by the following combination of characteristics as described in Table 1.

TABLE 1

| Characteristic | 'BG-12.3241' | 'INSPIRE' (U.S. Plant Pat. No. 29,794) |
|---|---|---|
| Fruit: color | Red | Orange red |
| Fruit: season average size (gm) | 27.7 | 26.6 |
| Terminal leaflet: shape of base | Obtuse | Acute |
| Foliage: number of leaflets | Ranges from 3 to 4 | 3 |
| Foliage: shape in cross section | Slightly concave to flat | Flat to slightly convex |
| Petiole: size (cm) | 12.0 | 10.2 |
| Petiole: pubescence | Heavy | Moderate |
| Stipule: anthocyanin intensity | Medium | Absent or very weak |
| Fruiting truss: position relative to foliage | Ranges from level with to above | Above |

For identification, a series of molecular markers have been determined for this new variety.

'BG-12.3241' differs from its parents, 'BG-6.3001' and 'BG-959' by the following combination of characteristics as described in Tables 2 and 3.

TABLE 2

| Characteristic | 'BG-12.3241' | 'BG-6.3001' (unpatented) |
|---|---|---|
| Fruit: market yield season | Ranges from medium to low | Medium |
| Fruit: firmness of flesh | Very firm | Medium |
| Fruit: flavor | Very good | Good |
| Plant: size | Medium | Ranges from medium to large |

TABLE 3

| Characteristic | 'BG-12.3241' | 'BG-959' (U.S. Plant Pat. No. 17,864) |
|---|---|---|
| Fruit: market yield season | Ranges from medium to low | Low |
| Fruit: color | Red | Dark red |
| Fruit: flavor | Very good | Good |
| Fruit: firmness of flesh | Very firm | Medium |

BRIEF DESCRIPTION OF THE PHOTOGRAPHS

The accompanying color photographs illustrate the overall appearance of typical specimens of the new strawberry variety 'BG-12.3241' at various stages of development, as true as it is reasonably possible with color reproductions of this type. Color in the photographs may differ slightly from the color value cited in the botanical descriptions which accurately describe the color of 'BG-12.3241'. The depicted plant and plant parts of the new strawberry variety 'BG-12.3241' are approximately six months old. The photographs were taken in Ventura County, Calif.

DETAILED BOTANICAL DESCRIPTION

Figure 1:
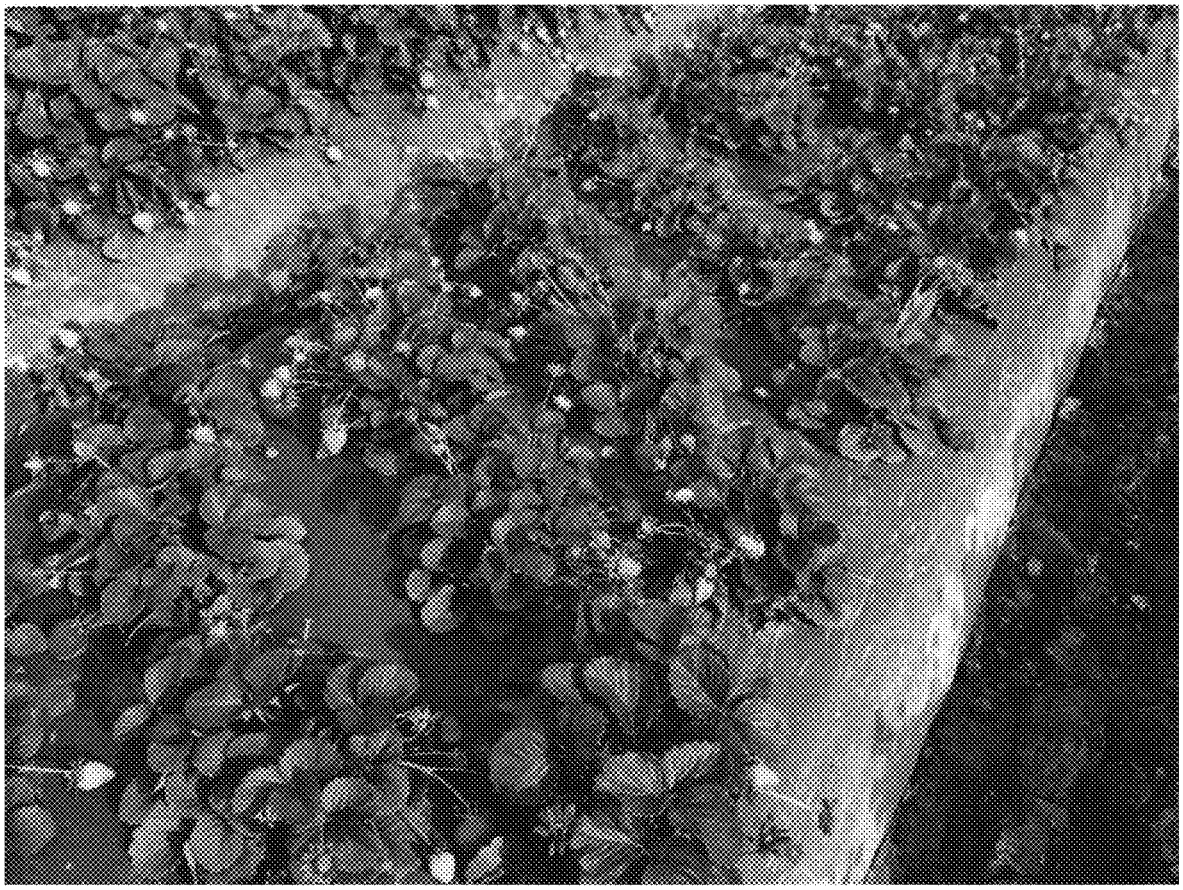
FIG. 1 shows fruiting field characteristics of 'BG-12.3241', taken in the month of April 2020.
Figure 2:
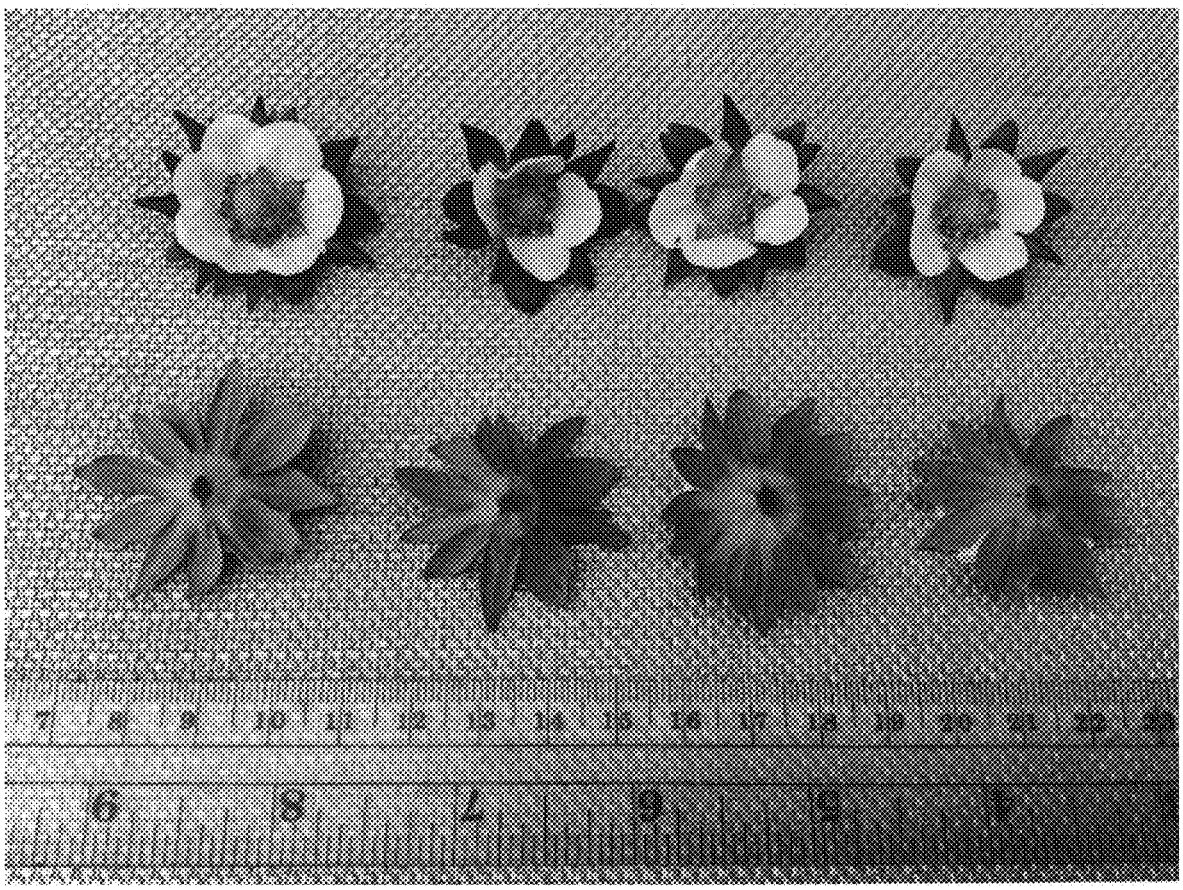
FIG. 2 shows upper and lower surfaces of flower and flower parts of 'BG-12.3241', taken in the month of April 2020.
Figure 3:
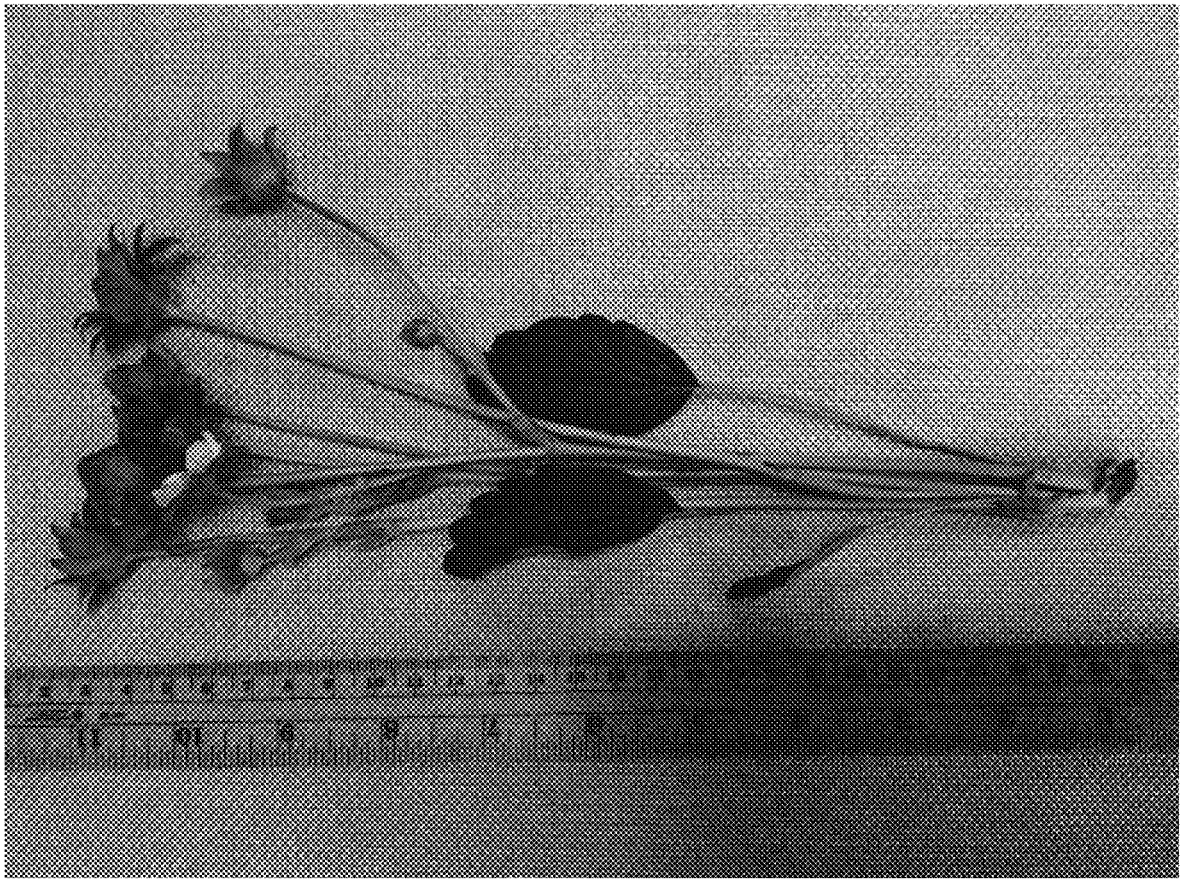
FIG. 3 shows typical fruiting truss and truss parts of 'BG-12.3241', taken in the month of April 2020.
Figure 4:
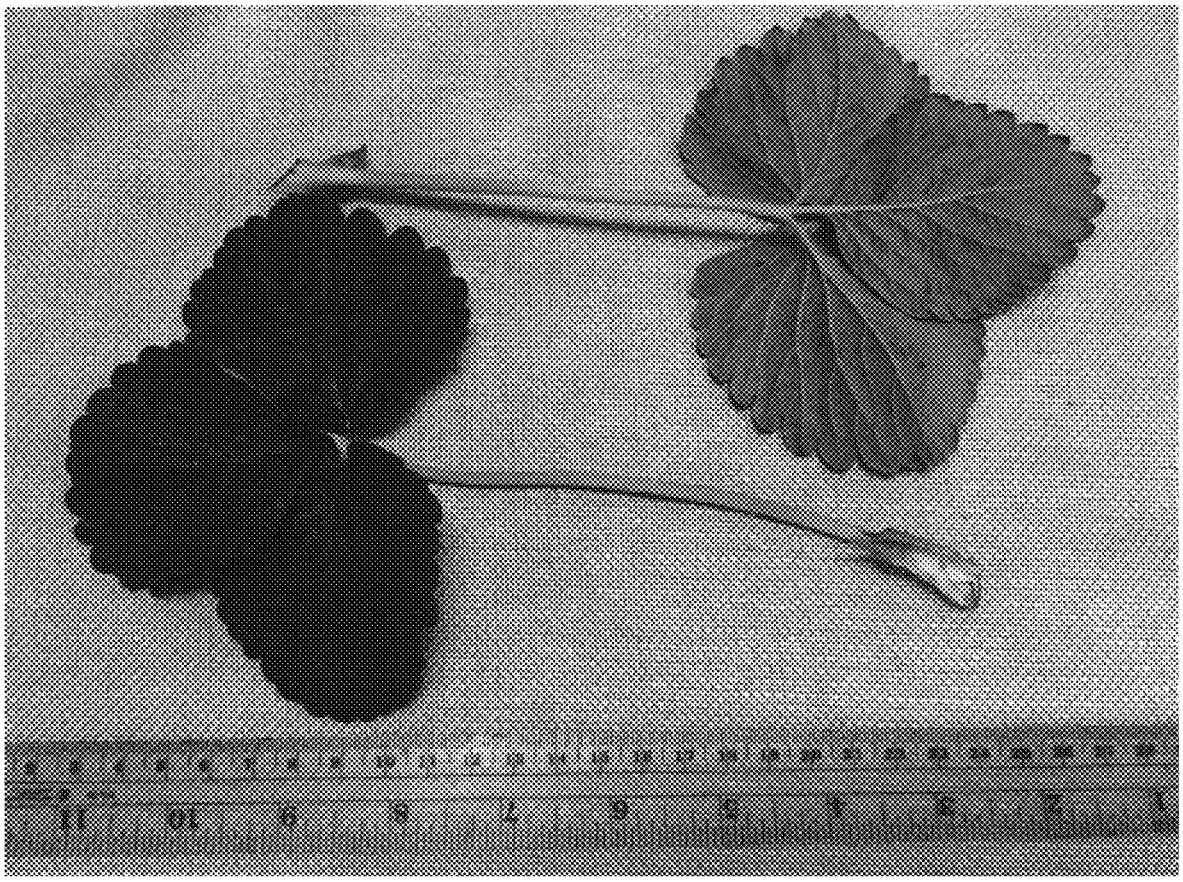
FIG. 4 shows upper and lower surfaces of leaf and leaf parts of 'BG-12.3241', taken in the month of April 2020.
Figure 5:
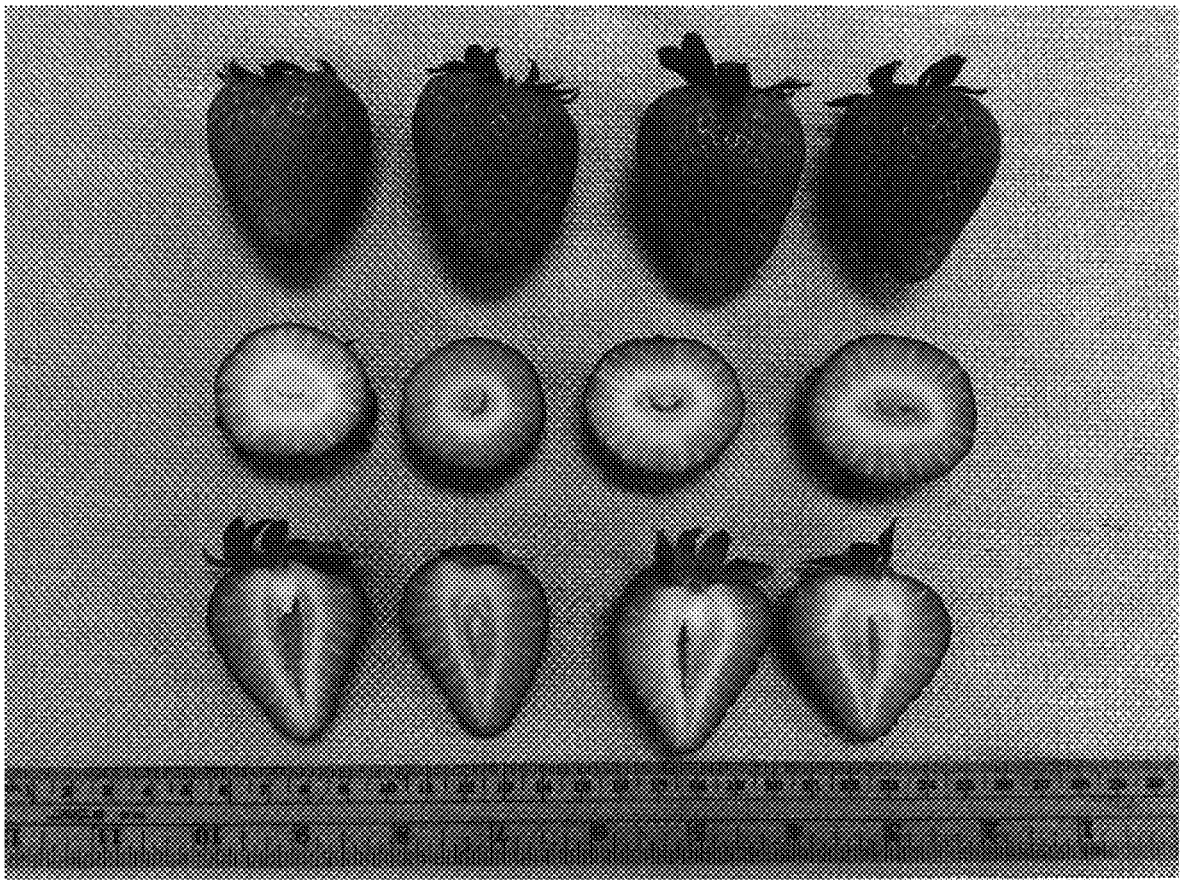
FIG. 5 shows internal and external mature fruit characteristics of 'BG-12.3241', taken in the month of April 2020.

The new variety 'BG-12.3241' has not been observed under all possible environmental conditions. The characteristics of the new variety 'BG-12.3241' may vary in detail, depending upon variations in environmental factors, including weather (temperature, humidity and light intensity), day length, soil type and location. In addition, the characteristics of any parental variety or comparison variety included in Tables 1, 2 and 3 of the present invention may vary in detail, depending upon variations in environmental factors, including weather (temperature, humidity and light intensity), day length, soil type and location.

The aforementioned photographs, together with the following description of the new variety 'BG-12.3241', unless otherwise noted, are based on observations taken during the 2020 growing season in Ventura County, Calif. These measurements and ratings were taken from plants of 'BG-12.3241' dug from a high-elevation nursery located in Siskiyou County, Calif. during early October 2019 and planted approximately four to five days later in Ventura County, Calif. The approximate age of the observed plants is five to six months. Yield observations including average weight and marketable yield, along with fruit quality characteristics including soluble solids, are averaged from five years of data collected from the 2016 through 2020 growing seasons. Flower measurements and characteristics are from secondary flowers unless otherwise noted. Fruit characteristics and measurements are from secondary fruit, unless otherwise noted.

Where noted, color terminology follows The Royal Horticultural Society Colour Chart, London (2007).

The following characteristics describe fruit, plant, stolon, foliage, fruiting truss, flower, reproductive organs and pest and disease characteristics of the new strawberry 'BG-12.3241'.

Fruit characteristics:

*Color of mature fruit.*—RHS 46B (red).

*Color of internal flesh (excluding core).*—RHS 44C (medium red).

*Color of core.*—RHS 39A (medium red).

*Average length (cm).*—4.5.

*Average width (cm).*—3.8.

*Size.*—Medium.

*Average length/width ratio.*—1.17 (slightly longer than broad).

*Fruit core cavity length (mm).*—19.8.

*Fruit core cavity width (mm).*—4.2.

*Average calyx diameter (cm).*—4.2.

*Season average weight (gm).*—27.7.

*Achene color, shaded side.*—RHS 153B (yellow green group).

*Achene color, sun-exposed side.*—RHS 184A (greyed purple group).

*Average achene weight (mg).*—0.60.

*Average achenes per berry.*—351.

*Marketable yield season (gm/plant).*—850.

*Predominant shape.*—Cordate (cordiform).

*Difference in shape between primary and secondary fruit.*—Slight.
*Band without achenes.*—Narrow.
*Evenness of surface.*—Even or very slightly uneven.
*Evenness of color.*—Even or very slightly uneven.
*Glossiness.*—Medium.
*Insertion of achenes.*—Level with surface.
*Position of calyx attachment.*—Level.
*Attitude of sepals.*—Outward.
*Size of calyx in relation to fruit diameter.*—Slightly larger.
*Adherence of calyx* (*when fully ripe*).—Strong.
*Firmness of flesh.*—Very firm.
*Distribution of red color of the flesh.*—Marginal and central.
*Hollow center expression.*—Moderate.
*Flavor.*—Very good.
*Soluble solids* (*% Brix*).—9.7.
*Flowering season* (*50% of plants with at least one flower*).—Medium (December in Ventura County, Calif.).
*Maturing season* (*50% of plants with mature fruit.*—Medium (January in Ventura County, Calif.).
*Harvest period.*—January to May (in Ventura County, Calif.).
*Harvest maturity.*—Mid-season (in Ventura County, Calif.).
*Type of bearing.*—Not remontant.

Plant characteristics:
*Average height* (*cm*).—17.6.
*Average spread* (*cm*).—29.5.
*Size.*—Medium.
*Habit.*—Upright.
*Density.*—Ranges from sparse to medium.
*Vigor.*—Medium.

Stolon characteristics:
*Color.*—RHS 146C (yellow green group).
*Anthocyanin coloration.*—RHS 184A (greyed purple group).
*Anthocyanin intensity.*—Strong.
*Pubescence.*—Medium.
*Attitude of hairs.*—Upward.
*Average quantity in nursery* (*per square foot*).—5 to 6 (medium).
*Average diameter at first bract* (*mm*).—3.1 (ranges from thin to medium).
*Length from mother plant to first daughter* (*cm*).—31.8.

Terminal leaflet characteristics:
*Average length* (*cm*).—7.5.
*Average width* (*cm*).—6.3.
*Average area terminal* ($cm^2$).—47.7.
*Average length/width ratio.*—1.19 (longer than broad).
*Shape of base.*—Obtuse.
*Margins* (*shape of teeth*).—Rounded (crenate).
*Average serrations per leaf.*—19.0.

Foliage characteristics:
*Color of upper surface.*—RHS 137A (medium yellow green).
*Color of underside.*—RHS 147C (yellow green group).
*Number of leaflets.*—3 to 4.
*Leaf size.*—Medium.
*Average length* (*cm*).—10.3.
*Average width* (*cm*).—13.4.
*Average area foliage* ($cm^2$).—138.2.
*Shape in cross section.*—Slightly concave to flat.
*Interveinal blistering.*—Medium.
*Leaf glossiness.*—Medium.
*Leaf variegation.*—Absent.

Petiole characteristics:
*Petiole color.*—RHS 145A (yellow green group).
*Average length* (*cm*).—12.0.
*Average diameter* (*mm*).—3.3.
*Petiolule color.*—RHS 145A (yellow green group).
*Petiolule average length* (*mm*).—6.9.
*Attitude of hairs.*—Strongly outward.
*Frequency of bract leaflets.*—Few (27% occurrence).
*Size of bract leaflets.*—N/A.
*Pubescence.*—Heavy.

Stipule characteristics:
*Color.*—RHS 146C (yellow green group).
*Anthocyanin coloration.*—RHS 59D (red purple group).
*Anthocyanin intensity.*—Medium.
*Average length* (*mm*).—12.9.
*Average width* (*mm*).—8.3.

Fruiting truss characteristics:
*Anthocyanin coloration.*—RHS 181A (greyed red group).
*Anthocyanin intensity.*—Strong.
*Average length at maturity* (*cm*).—24.2.
*Position relative to foliage.*—Ranges from level with to above.
*Flower quantity* (*season average per plant*).—35 to 40 (medium).
*Pedicel attitude of hairs.*—Slightly outward.
*Pubescence.*—Medium.
*Attitude at first pick.*—Prostrate.

Flower characteristics:
*Petal color.*—RHS NN155C (white group).
*Sepal color.*—RHS N137A (green group).
*Corolla* (*flower*) *average diameter* (*mm*).—26.6 (medium).
*Calyx average diameter* (*mm*).—35.0.
*Petal average length* (*mm*).—10.5.
*Petal average width* (*mm*).—10.0.
*Petal average length/width ratio.*—1.05 (longer than broad).
*Average petals per flower.*—5.5.
*Sepal average length* (*mm*).—13.8.
*Sepal average width* (*mm*).—5.5.
*Sepal average length/width ratio.*—2.50.
*Average sepals per flower.*—11.3.
*Size of calyx relative to corolla.*—Larger.
*Size of inner calyx relative to outer calyx.*—Ranges from same to larger.
*Relative position of petals* (*flowers with 5 or 6 petals*).—Overlapping.

Reproductive organs:
*Receptacle/ovary color.*—RHS 147C (yellow green group).
*Anther/pollen color.*—RHS 14A (yellow orange group).
*Stamen.*—Present.
*Pollen amount.*—Abundant.

Disease and pest reactions:
*Powdery mildew* (*Sphaerotheca macularis*).—Moderately resistant.
*Angular leaf spot* (*Xanthomonas fragariae*).—Moderately susceptible.
*Botrytis fruit rot* (*Botrytis cinerea*).—Moderately susceptible.

*Fusarium wilt* (*Fusarium oxysporum*).—Susceptible.

*Anthracnose crown rot* (*Colletotrichum fragariae*).—Susceptible.

*Two-spotted spider mite* (*Tetranychus urticae*).—Moderately susceptible.

We claim:

1. A new and distinct strawberry plant named 'BG-12.3241', as herein described and illustrated.

* * * * *